US010441525B2

(12) United States Patent
Pang et al.

(10) Patent No.: US 10,441,525 B2
(45) Date of Patent: Oct. 15, 2019

(54) COSMETIC COMPOSITION CONTAINING THERMOPLASTIC ELASTOMER AND SEMI-CRYSTALLINE POLYMER

(71) Applicant: L'ORÉAL, Paris (FR)

(72) Inventors: Christopher Pang, New York, NY (US); Hy Si Bui, Piscataway, NJ (US)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 15/138,073

(22) Filed: Apr. 25, 2016

(65) Prior Publication Data

US 2017/0304180 A1  Oct. 26, 2017

(51) Int. Cl.
A61K 8/81 (2006.01)
A61Q 1/10 (2006.01)
A61K 8/31 (2006.01)
A61K 8/90 (2006.01)

(52) U.S. Cl.
CPC .............. A61K 8/8152 (2013.01); A61K 8/31 (2013.01); A61K 8/90 (2013.01); A61Q 1/10 (2013.01); A61K 2800/594 (2013.01)

(58) Field of Classification Search
CPC ............ A61K 8/8152; A61K 2800/594; A61K 8/8117; A61K 8/90; A61Q 1/10
See application file for complete search history.

(56) References Cited

U.S. PATENT DOCUMENTS

| | | | |
|---|---|---|---|
| 5,519,063 A | 5/1996 | Mondet et al. | |
| 6,274,131 B1 | 8/2001 | Piot et al. | |
| 6,482,400 B1 | 11/2002 | Collin | |
| 6,517,823 B1 | 2/2003 | Norman et al. | |
| 7,582,719 B1 | 9/2009 | Tan et al. | |
| 7,871,634 B2 | 1/2011 | Feng | |
| 7,884,158 B2 | 2/2011 | Bui et al. | |
| 8,211,416 B2 | 7/2012 | Narebski et al. | |
| 8,313,735 B2 | 11/2012 | McDermott | |
| 8,526,499 B2 | 9/2013 | Jeon et al. | |
| 8,557,230 B2 | 10/2013 | Bui et al. | |
| 8,673,282 B2 | 3/2014 | Bui et al. | |
| 8,673,283 B2 | 3/2014 | Bui et al. | |
| 8,673,284 B2 | 3/2014 | Bui et al. | |
| 8,715,634 B2 | 5/2014 | Atis | |
| 8,758,739 B2 | 6/2014 | Bui et al. | |
| 8,778,323 B2 | 7/2014 | Bui et al. | |
| 8,932,573 B2 | 1/2015 | Alden-Danforth et al. | |
| 9,040,593 B2 | 5/2015 | Bui et al. | |
| 2005/0287093 A1 | 12/2005 | Lebre et al. | |
| 2005/0287100 A1* | 12/2005 | Lebre ....................... | A61K 8/31 424/70.16 |
| 2007/0183997 A9 | 8/2007 | Lebre et al. | |
| 2007/0258923 A1 | 11/2007 | Bui et al. | |
| 2007/0258924 A1 | 11/2007 | Bui et al. | |
| 2007/0258925 A1 | 11/2007 | Bui et al. | |
| 2007/0258932 A1 | 11/2007 | Bui et al. | |
| 2007/0258933 A1 | 11/2007 | Bui et al. | |
| 2007/0258934 A1 | 11/2007 | Bui et al. | |
| 2008/0102048 A1 | 5/2008 | McDermott | |
| 2008/0102049 A1 | 5/2008 | McDermott | |
| 2008/0175808 A1* | 7/2008 | Pavel ................... | A61K 8/8111 424/70.7 |
| 2010/0028284 A1 | 2/2010 | Atis et al. | |
| 2010/0208817 A1 | 8/2010 | Jeon et al. | |
| 2010/0297041 A1 | 11/2010 | Smith et al. | |
| 2011/0243864 A1 | 10/2011 | Farcet et al. | |
| 2013/0188713 A1 | 7/2013 | Jeon et al. | |
| 2013/0236409 A1 | 9/2013 | Bui et al. | |
| 2015/0265519 A1 | 9/2015 | Bui et al. | |

FOREIGN PATENT DOCUMENTS

EP     0 550 745     7/1993

OTHER PUBLICATIONS

Air Products (http://www.bisi.cz/cmsres.axd/get/cms$7CVwRhc3U SVqgzxkKF96gl$2BPpOqbtVs75HRTjLxXUpZvBPQ97RI1thTexl Hls7NqNufgyMPfh7fnpaFiNEaHYRNw$3D$3D) available 2008, pp. 1-81 (Year: 2008).*
International Search Report and Written Opinion dated Aug. 29, 2017 in PCT/US2017/027855.

* cited by examiner

Primary Examiner — Andrew S Rosenthal
(74) Attorney, Agent, or Firm — Oblon, McClelland, Maier & Neustadt, L.L.P.

(57) ABSTRACT

The present invention relates to a cosmetic composition comprising a thermoplastic elastomer, a semi-crystalline polymer and an organic solvent. The compositions of the present invention may optionally contain at least one colorant. The invention also relates to a method for making up and/or enhancing the appearance of a keratinous substrate, in particular lashes, by applying these compositions to the keratinous substrate.

11 Claims, No Drawings

COSMETIC COMPOSITION CONTAINING THERMOPLASTIC ELASTOMER AND SEMI-CRYSTALLINE POLYMER

TECHNICAL FIELD

The present invention relates to a cosmetic composition and method for making up and/or enhancing the appearance of a keratinous substrate, comprising at least one thermoplastic elastomer, at least one semi-crystalline polymer and at least one organic solvent. The compositions of the present invention may optionally contain at least one colorant.

BACKGROUND OF THE INVENTION

Makeup products, especially mascaras, are expected to have long wear, transfer resistance properties and most importantly provide good curling to eyelashes.

With regard to this expectation, currently marketed curling mascaras are typically emulsions comprised of water and a high amount of waxes (from 10-25%), specifically hard waxes. To enhance the desired properties, the mascaras often contain one or more film forming polymers and combinations of different waxes.

Illustrations of polymers and waxes employed in typical mascara compositions are presented in U.S. Pat. Nos. 6,517,823, 6,274,131, 6,482,400 and US2010/0028284. However, the above-mentioned polymers and waxes, which are advantageous in providing the desired properties, make the finished products to be difficult to spread and deliver an unfavourable tacky feeling.

The inventors have found that the combination of a thermoplastic elastomer and a semi-crystalline polymer in an organic solvent and in the absence of water and hard waxes, provides a good curl (lift) which is stable over time.

While the use of thermoplastic elastomers and semi-crystalline polymers has previously been discussed, for example in U.S. Pat. Nos. 7,884,158, 8,211,416, US2008/0175808 and US2015/0265519, the inventors have established that the association of di-block or/and tri-block thermoplastic elastomers having double glass transition temperatures (Tg) and semi-crystalline polymer with melting temperature higher than 45° C., yields a composition having an exceptional curling effect.

BRIEF SUMMARY OF THE INVENTION

The present invention relates to homogeneous cosmetic compositions for making up and/or enhancing the appearance of keratinous substrates comprising:
  (a) at least one thermoplastic elastomer;
  (b) at least one semi-crystalline polymer; and
  (c) at least one organic solvent According to another aspect of the present invention, there is provided a method of making up and/or enhancing the appearance of a keratinous substrate, in particular eye lashes, comprising applying onto the keratinous substrate the above-disclosed composition, wherein the composition provides a great curl.

It is to be understood that both the foregoing general description and the following detailed description are exemplary and explanatory only, and are not restrictive of the invention.

DESCRIPTION OF THE INVENTION

In the following description of the invention and the claims appended hereto, it is to be understood that the used terms have their ordinary and accustomed meanings in the art, unless otherwise specified.

"About" as used herein means within 10% of the indicated number (e.g. "about 10%" means 9%-11% and "about 2%" means 1.8%-2.2%).

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"At least one" means one or more and thus includes individual components as well as mixture/combinations.

The term "glass transition temperature" (Tg) generally refers to the temperature at which amorphous material changes from a glassy solid state to a rubbery state. The temperature may be measured by standard techniques in the art, such a Differential Scanning Calorimetry (DSM), e.g., according to a standard protocol such as ASTM D3418-97 standard.

"Keratinous substrate" may be chosen from, for example, hair, eyelashes, lip, and eyebrows, especially eye lashes.

"Low Tg" or "Low Glass Transition Temperature" as used herein to describe the polymeric substances characterized by glass transition temperature (Tg) of lower than from about 6° C.

"High Tg" or "High Glass Transition Temperature" as used herein to describe the polymeric substances characterized by glass transition temperature (Tg) of from about 6° C. or higher.

"Polymers" as defined herein, include homopolymers and copolymers formed from at least two different types of monomers.

"The "Curling" or "curl" or "lift" of eyelashes as used herein, refers to a lifting and bending effect achieved after application of mascara compositions or other cosmetics and care treatments.

"Anhydrous" or "water free" of "substantially water free", used interchangeably herein, means that the composition contains no more than 5% of water.

"Wax free" or "essentially free of wax" or "devoid of wax" or "free of wax" used interchangeably herein, mean that composition may contain no more than about 3% of wax.

The compositions and methods of the present invention can comprise, consist of, or consist essentially of the essential elements and limitations of the invention described herein, as well as any additional or optional ingredients, components, or limitations described herein or otherwise useful.

In an embodiment, the invention relates to a mascara composition comprising:
  at least one thermoplastic elastomer;
  at least one semi-crystalline polymer; and
  at least one organic solvent;
wherein the ratio of at least one thermoplastic elastomer to the at least one semi-crystalline polymer is from about 5:1 to about 4:1, from about 2:1 to about 6:1 and from about 0.8:1 to about 0.4:1, by weight, relative to the total weight of the composition. All numerical values are weight percent solids (actives).

In the particular embodiment, the invention relates to an anhydrous mascara composition comprising:
  from about 0.5% to about 80% of at least one thermoplastic elastomer;
  from about 0.1% to about 20% of at least one semi-crystalline polymer; and from about 4% to about 99% of at least one organic solvent.

Another embodiment of this invention relates to a mascara composition comprising:

from about 0.5% to about 80% of at least one di-block thermoplastic elastomer;

from about 0.1% to about 20% of at least one semi-crystalline polymer; and from about 4% to about 99% of at least one organic solvent.

The invention also relates to an anhydrous curling mascara composition essentially free of wax.

Another aspect of the invention relates to a method of making the inventive composition.

Semi-Crystalline Polymers

The cosmetic composition of the invention includes at least one semi-crystalline polymer.

The term "semi-crystalline polymer" is used to mean polymers having a crystallizable portion, a crystallizable pendant chain, or a crystallizable sequence in its backbone, and an amorphous portion in the backbone, and that also presents a first-order reversible change-of-phase temperature, in particular for melting (solid-liquid transition). When the crystallizable portion is in the form of a crystallizable sequence of the polymer backbone, the amorphous portion of the polymer is in the form of an amorphous sequence. The semi-crystalline polymer is then a sequenced copolymer, e.g. of the diblock, triblock, or multiblock type, having at least one crystallizable sequence and at least one amorphous sequence. The term "sequence" generally means at least five identical repetition motifs. The crystallizable sequence(s) is/are then of a chemical nature that is different from the amorphous sequence(s).

The semi-crystalline polymer has a melting temperature greater than or equal to 30 degrees centigrade, in particular lying in the range 30 degrees centigrade to 100 degrees centigrade, preferably in the range 30 degrees centigrade to 80 degrees centigrade. The melting temperature is a first-order change-of-state temperature.

This melting temperature may be measured by any known method, and in particular by using differential scanning calorimetry (DSC).

Additionally, the semi-crystalline polymer applicable in this invention has molecular weight (MW) from about 30,000 (g/mol) to about 200,000 (g/mol).

The at least one semi-crystalline polymer may be employed in the cosmetic composition of the present invention in an amount ranging from about 0.1 to about 20 percent by weight, or from about 0.5 to about 10 percent by weight, or from about 1 to about 5 percent by weight, relative to the total weight of the composition, including all ranges and subranges there between.

By way of examples, such polymers are described in EP 1 396 259 and U.S. Pat. No. 8,980,240, the entire content of which are hereby incorporated by the references.

Semi-crystalline polymers containing crystallizable side chains may be homopolymers or copolymers comprising from 50 percent to 100 percent by weight of units resulting from the polymerization of one or more monomers bearing a crystallizable hydrophobic side chain.

Particularly suitable examples of semi-crystalline polymers useful in this invention are described in U.S. Pat. No. 8,932,573, the entire content of which is hereby incorporated by the references.

Polymers bearing in the skeleton at least one crystallizable block are especially block copolymers consisting of at least two blocks of different chemical nature, one of which is crystallizable. Examples are block copolymers of olefin or of cycloolefin containing a crystallizable chain, and copolymers containing at least one crystallizable block, the rest of the copolymer being amorphous (at room temperature). These copolymers may also contain two crystallizable blocks of different chemical nature.

In particular exemplary embodiments, the polymer comes from a crystallizable chain monomer selected from C14 to C30 saturated alkyl(meth)acrylates, including poly C10-30 alkyl(meth)acrylates.

Suitable examples of semi-crystalline alkyl(meth)acrylates include, but are not limited to, the Intelimer® or Doresco® products from the company Landec, such as those described in the brochure "Intelimer® Polymers" and/or are disclosed in U.S. patent application publication nos. 2006/0292095 and 2006/0263438, the disclosure of both of which is hereby incorporated by reference in their entirety. Specific examples include:

Doresco/Intelimer IPA 13-1®: polystearyl acrylate, with melting point of 49 degrees centigrade (° C.) and molecular weight (MW) of 145,000; and Doresco/Intelimer IPA 13-6': polybehenyl acrylate, having melting point of 66 degrees centigrade (° C.) and molecular weight (MW) of 45,000-126,000 g/mol.

In accordance with the present invention, it is also possible to use the semi-crystalline polymers obtained by copolymerization of stearyl acrylate and of acrylic acid or of NVP, or by copolymerization of behenyl acrylate and of acrylic acid or NVP, as described in document U.S. Pat. No. 5,519,063 or EP-A-0 550 745, the entire contents of both of which are hereby incorporated by reference.

The at least one semi-crystalline polymer, poly C10-30 alkyl acrylate may be employed in the cosmetic composition of the present invention in an amount ranging from about 0.1 to about 20 percent by weight, or from about 0.5 to about 10 percent by weight, or from about 1 to about 5 percent by weight, relative to the total weight of the composition, including all ranges and subranges there between.

Applicable examples of semi-crystalline polymers useful in this invention are hyperbranched polymers, including hyperbranched functional polymer and these disclosed in US2015/0265519, the entire contents of which is hereby incorporated by the reference.

Generally, hyperbranched polymers are molecular constructions having a branched structure, generally around a core. Their structure generally lacks symmetry, the base units or monomers used to construct the hyperbranched polymer can be of diverse nature and their distribution is non-uniform. The branches of the polymer can be of different natures and lengths. The number of base units, or monomers, may be different depending on the different branching. While at the same time being asymmetrical, hyperbranched polymers can have any of the following: an extremely branched structure around a core; successive generations or layers of branching; layer of end chains.

According this invention, particularly useful are Hyperbranched Polyacids.

In a preferred embodiment, the compositions of the invention comprise at least one hyperbranched polyacid. Hyperbranched polyacid refers to the fact the functional groups of the hyperbranched functional polymer are substituted with carboxylic acid groups.

The at least one hyperbranched polyacid compound of the present invention has at least two carboxyl groups. Preferably, the hyperbranched polyacid has a carboxyl number of at least 3, more preferably of at least 10, more preferably of at least 50, and more preferably of at least about 150.

According to preferred embodiments, the at least one hyperbranched polyacid has a carboxyl number between 50 and 250, preferably between 75 and 225, preferably between 100 and 200, preferably between 125 and 175, including all ranges and subranges there between such as 90 to 150.

Suitable examples of hyperbranched polyacids can be found in U.S. Pat. No. 7,582,719 and US2013/0236409, the entire contents of which are hereby incorporated by reference.

In an embodiment the hyperbranched polyacid is a semi-crystalline polymer having a glass transition temperature (Tg) of from about −30° C. to about 0° C., particularly from about −20° C. to about −1° C., more typically from about −15° C. to about −5° C., and a melting point of from about 45° C. to about 100° C., typically from about 50° C. to about 90° C., most typically from about 55° C. to about 85° C.

A particularly preferred acid functional olefinic polymer is C30+ olefin/undecylenic acid copolymer available from New Phase Technologies under trade name Performa V™-6112.

The at least one hyperbranched polymer, in including at least one hyperbranched polyacid polymer may be present in the composition of the invention in an amount ranging from about 0.5% to about 10% by weight, more particularly from about 1% to about 8% by weight, most particularly from about 2% to about 6% by weight, including all ranges and subranges therebetween, relative to the total weight of the composition.

According to another embodiment of this invention, suitable semi-crystalline polymers are polyamide resins, as these disclosed in U.S. Pat. Nos. 8,715,634 and 7,871,634, the entire contents of which are hereby incorporated by the references.

Specifically, the disclosed polymers are ester-terminated polyamides represented by the following formula (I):

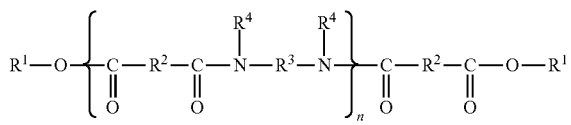

in which:

n is an integer which represents the number of amide units such that the number of ester groups present in the structuring polymer ranges from 10 percent to 50 percent of the total number of all the ester groups and all the amide groups comprised in the structuring polymer (e.g., n may be an integer ranging from 1 to 5, for example, an integer ranging from 3 to 5);

$R^1$, which are identical or different, are each chosen from alkyl groups comprising at least 4 carbon atoms and alkenyl groups comprising at least 4 carbon atoms (e.g., each can be chosen from C12 to C22 alkyl groups, such as from C16 to C22 alkyl groups);

$R^2$, which are identical or different, are each chosen from C4 to C42 hydrocarbon-based groups with the proviso that at least 50 percent of $R^2$ are chosen from C30 to C42 hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, C1 to C10 alkyl groups and a direct bond to group chosen from $R^3$ and another $R^4$ such that when the at least one group is chosen from another $R^4$, the nitrogen atom to which both $R^3$ and $R^4$ are bonded forms part of a heterocyclic structure defined in part by $R^4$—N—$R^3$, with the proviso that at least 50 percent of all $R^4$ are chosen from hydrogen atoms.

Non-limiting examples of at least one polyamide polymer that may be used in the compositions of the present invention include the commercial products sold by Arizona Chemical under the names UNICLEAR® 80 and UNICLEAR® 100. These are sold, respectively, in the form of an 80 percent (in terms of active material) gel in a mineral oil and a 100 percent (in terms of active material) gel.

Another example of the ester-terminated polyamides is commercially available from Arizona Chemical under the name UNICLEAR® VG (INCI Name: Ethylenediamine/stearyl dimer dilinoleate copolymer) and OLEOCRAFT™ from Croda (INCI Name) Ethylenediamine/stearyl dimer dilinoleate copolymer).

Preferably, the at least one polyamide resin is present in an amount ranging from about 0.5 percent to about 20 percent by weight of active material with respect to the total weight of the composition, more preferably from about 2 percent to about 10 percent, more preferably from about 3 percent to about 6 percent, by weight of active material with respect to the total weight of the composition, including all ranges and subranges there between.

Thermoplastic Elastomers (Block Copolymer)

The thermoplastic elastomers of the present invention are block copolymers that are characterized by the presence of at least one "hard" segment, and at least one "soft" segment. Aside from their compositional nature, the hard and soft segments of the block copolymers of the present invention are defined in terms of their respective glass transition temperatures (Tg). More particularly, the hard segment has a Tg of 50 degrees centigrade or more, whereas the soft segment has a Tg of 0 degrees centigrade or less.

The glass transition temperature Tg for the hard block can range from 50 degrees centigrade to 150 degrees centigrade; 60 degrees centigrade to 125 degrees centigrade; 70 degrees centigrade to 120 degrees centigrade; 80 degrees centigrade to 110 degrees centigrade.

The glass transition temperature Tg for the soft segment of the block copolymer can range from 0 degrees centigrade to −150 degrees centigrade; −10 degrees centigrade to −125 degrees centigrade; −25 to −100 degrees centigrade.

A more in depth explanation can be found in U.S. Pat. Nos. 5,294,438 and 6,403,070, the entire contents of which are hereby incorporated by reference.

The hard segments of the thermoplastic elastomer typically comprise vinyl monomers in varying amounts. Examples of suitable vinyl monomers include, but are not limited to styrene, methacrylate, acrylate, vinyl ester, vinyl ether, vinyl acetate, and the like.

Thermoplastic elastomers useful in the present invention are block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

According to this invention, particularly useful are thermoplastic elastomers disclosed in U.S. Pat. Nos. 7,884,158 and 9,040,593, the entire contents of which are hereby incorporated by references.

In preferred embodiments, the at least one thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene.

The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon® (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Particularly useful for this invention are hydrogenated styrene/butadiene copolymer (Kraton™ G1657) and hydrogenated styrene/isoprene copolymer (Kraton™ G1701), both commercially available from Kraton™ Polymers.

Preferably, the at least one thermoplastic elastomer resin is present in an amount ranging from about 0.5 percent to about 80 percent by weight of active material with respect to the total weight of the composition, more preferably from about 1 percent to about 60 percent, more preferably from about 2 percent to about 40 percent, and most preferably from about 3 percent to about 10 percent by weight of active material with respect to the total weight of the composition, including all ranges and subranges there between.

Organic Solvent

The composition of the invention also comprises a cosmetically acceptable solvent typically selected from a cosmetically acceptable organic solvent. Preferred organic solvents are non-aromatic oils such as, for example, non-aromatic hydrocarbon-based oils and non-aromatic silicone oils. In one embodiment, the non-aromatic oil is a volatile oil.

As used herein, the term "volatile oil" means an oil that is capable of evaporating on contact with keratin materials in less than one hour, at approximately room temperature and atmospheric pressure (760 mmHg). Volatile oils that may be used according to the disclosure include, but are not limited to, volatile cosmetic oils, which are liquid at room temperature and have a non-zero vapor pressure at room temperature and atmospheric pressure, said vapor pressure ranging, for example, from about 0.13 Pa to about 40,000 Pa (10-3 to 300 mmHg), such as from about 1.3 Pa to about 13,000 Pa (0.01 to 100 mmHg), or from about 1.3 Pa to about 1,300 Pa (0.01 to 10 mmHg). In contrast, non-volatile oils have a vapor pressure of less than about 1.33 Pa (0.01 mmHg).

According to various embodiments, the non-aromatic hydrocarbon-based oils may be chosen from:

hydrocarbon-based oils comprising from 8 to 16 carbon atoms, for example, C8-C16 branched alkanes such as C8-C16 isoalkanes of petroleum origin (also known as isoparaffins), for instance isododecane (also known as 2,2,4,4,6-pentamethylheptane), isodecane, and isohexadecane, and, for example, the oils sold under the trade names Isopar® and Permethyl®; linear alkanes, for instance, n-dodecane (C12) and n-tetradecane (C14) sold by Sasol under the respective references Parafol® 12-97 and Parafol® 14-97, and mixtures thereof; the undecane-tridecane mixture, and mixtures of n-undecane (C11) and of n-tridecane (C13) obtained in Examples 1 and 2 of International Patent Application Publication No. WO 2008/155 059 assigned to the company Cognis, and mixtures thereof;

linear and branched hydrocarbons of mineral or synthetic origin, such as petroleum jelly, polydecenes, hydrogenated polyisobutene such as Parleam®, squalane, liquid paraffins, and mixtures thereof;

synthetic esters such as oils of formula $R'_1COOR'_2$ in which $R'_1$ is chosen from linear and branched fatty acid residues comprising from 1 to 40 carbon atoms and $R'_2$ is chosen from branched hydrocarbon-based chains comprising from 1 to 40 carbon atoms, with the proviso that $R'_1+R'_2 \geq 10$, for instance purcellin oil (cetostearyl octanoate), isopropyl myristate, isopropyl palmitate, octyl palmitate, C12 to C15 alkyl benzoate, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl and polyalkyl heptanoates, octanoates, decanoates, and ricinoleates such as propylene glycol dioctanoate; hydroxylated esters such as isostearyl lactate, diisostearyl malate, and 2-octyldodecyl lactate; polyol esters and pentaerythritol esters;

fatty alcohols that are liquid at room temperature, comprising a branched and/or unsaturated carbon-based chain comprising from 12 to 26 carbon atoms, for instance, octyldodecanol, isostearyl alcohol, oleyl alcohol, 2-hexyldecanol, 2-butyloctanol, and 2-undecylpentadecanol;

higher fatty acids such as oleic acid, linoleic acid, linolenic acid, and mixtures thereof;

hydrocarbon-based oils of plant origin such as triglycerides comprising fatty acid esters of glycerol, the fatty acids of which may have chain lengths comprising from 4 to 24 carbon atoms, these chains possibly being linear or branched, and saturated or unsaturated; for example, heptanoic and octanoic acid triglycerides, wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, *quinoa* oil, rye oil, safflower oil, candlenut oil, passion flower oil, and musk rose oil; shea butter; and caprylic/capric acid triglycerides, for instance those sold by the company Stéarineries Dubois or those sold under the names Miglyol 810®, 812® and 818® by the company Dynamit Nobel; and mineral oil.

According to one exemplary embodiment, the at least one non-aromatic oil is chosen from hydrocarbon-based oils comprising from 8 to 16 carbon atoms. For example, in at least one embodiment, the non-aromatic oil is selected from isodecane, isododecane, isohexadecane, and mixtures thereof.

The organic solvent may be present in the composition of the present invention in an amount ranging from about 4% to about 99% by weight, more preferably from about 10% to about 95% by weight, most preferably from about 15% to about 90% by weight, including all ranges and subranges there between, relative to the total weight of the composition.

Pigment(s)

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention, including but not limited to, surface treatments with compounds such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. In an embodiment of the invention the pigment is present in an amount from about 5% to about 15% by weight, more particularly about 7% by weigh based on the total weight of the composition.

Additional Optional Additive

A composition according to the invention may also comprise at least one agent usually used in cosmetics, chosen, for example, from: reducing agents; thickeners; film-forming agents that are especially hydrophobic, or are softeners, antifoams, moisturizers, or UV-screening agents; ceramides; cosmetic active agents; peptizers; fragrances; proteins; vitamins; propellants; hydrophilic or lipophilic, film-forming or non-film-forming polymers; lipophilic or hydrophilic gelling agents; and preservatives. Non-limiting examples of preservatives include phenoxyethanol and caprylyl glycol. A non-exhaustive listing of such ingredients is found in U.S. Pat. No. 7,879,316, the entire content of which is hereby incorporated by reference. Additional examples of additives may be found in the International Cosmetic Ingredient Dictionary and Handbook (9th ed. 2002, and subsequent editions).

In an embodiment, the composition includes at least one preservative selected from Phenoxyethanol, caprylyl glycol, and a mixture thereof.

If present, the above additives are typically found in an amount for each of them of between about 0.01% and about 10% by weight, most typically from about 0.5% to about 5% by weight, including all ranges and subranges there between, by weight relative to the total weight of the composition. A person skilled in the art will take care to select the constituents of the composition such that the advantageous properties associated with the invention are not, or are not substantially, adversely affected.

EXAMPLES

The following Examples are intended to be non-restrictive and explanatory only, with the scope of the invention being defined by the claims.

As used in herein INCI US stands for International Nomenclature of Cosmetic Ingredients US.

TABLE 1

Mascara Compositions

| INCI Name | control 1 | control 2 | inventive 1 | inventive 2 |
|---|---|---|---|---|
| DISTEARDIMONIUM HECTORITE | 0.166 | 0.17 | 0.166 | 0.166 |
| ISODODECANE | 75.504 | 74.5 | 70.504 | 65.504 |
| HYDROGENATED STYRENE/ISOPRENE COPOLYMER (KRATON ™ G1701) | 3.988 | 0 | 3.988 | 3.988 |
| TRIS-BHT MESITYLENE | 0.012 | | 0.012 | 0.012 |
| ISODODECANE | 11.5971 | 11.6 | 11.5971 | 11.5971 |

TABLE 1-continued

| Mascara Compositions | | | | |
|---|---|---|---|---|
| INCI Name | control 1 | control 2 | inventive 1 | inventive 2 |
| DISTEARDIMONIUM HECTORITE | 1.333 | 1.33 | 1.333 | 1.333 |
| PROPYLENE CARBONATE | 0.3999 | 0.4 | 0.3999 | 0.3999 |
| IRON OXIDES | 7 | 7 | 7 | 7 |
| POLY C10-30 ALKYL ACRYLATE (INTELIMER ® IPA 13-6 POLYMER) | 0 | 5 | 5 | 10 |

All numerical values in the above Table are weight percent active.

Method of Preparation of Mascaras

All ingredients were combined in a container, heated to 95° C. and placed in a speed mixer (DAC 150) and mixed at 2750 rpm for 5 minutes until homogeneous. The mixture was then cooled to room temperature while mixing with a propeller blade. The tested compositions were filled into mascara containers assembled with curved elastomeric brushes.

Assessment of curling effect of inventive compositions against controls and Comparative Mascaras.

The results of curling properties of the mascara compositions are reported in Table 1.

The curling properties of the inventive compositions were tested against two controls (control 1 and control 2 as disclosed in Table 1) and against two anhydrous comparative mascaras, comparator A having volumizing effect and comparator B providing curling. Below is the structure of both comparators.

Comparator A: petroleum distillates, polyethylene, disteardimonium hectorite, carnauba wax, trihydroxystearin, propylene carbonate, pentaerythrityl hydrogenated rosinate, tall oil glycerides, tocopheryl acetate, phenoxyethanol, panthenol, propylparaben, pigments.

Comparator B: isododecane, trimethylsiloxysilicate, disteardimonium hectorite, dextrin palmitate/ethylhexanoate, microcrystalline wax, beeswax, polyethylene, propylene carbonate, amellia *japonica* seed oil, *chamomilla recutita* (*matricaria*) extract, nylon-6, aluminum distearate, pentaerythrityl hydrogenated rosinate, octyldodecyl isostearate, glyceryl isostearates, triethoxysilylethyl polydimethylsiloxyethyl hexyl dimethicone, caprylic/capric triglyceride, diethylaminoethyl methacrylate/hema/perfluorohexylethyl, methacrylate crosspolymer, pigments In order to compare the curling properties of the tested compositions, the evaluated mascara products were manually applies to fake eye lashes made of natural hair fibers (each fiber was 12 mm long). One sample of handmade eye lashes was stroked 30 times with the tested product, using elastomeric curved brush.

The lift (curve) of eyelashes was captured by a camera a digital camera (Nikon D5500) and the angle of the lift was measured using a protractor. The angle values were correlated to a scale describing the curling effect of the tested mascaras, as described in Table 2. The images were taken for untreated lashes, immediately after application of the tested mascaras and 10 minutes after the treatment. The tests were conducted through one day at ambient conditions (room temperature 20-25° C. and 20-30% relative humidity).

TABLE 2

| Correlation between an angle of a curl and a scale describing the curling effect | | |
|---|---|---|
| Lift (curl) rating | Scale | Angle ° |
| none | 1 | 0-5 |
| slight | 2 | 6-10 |
| medium | 3 | 11-15 |
| good | 4 | 16-20 |
| great | 5 | 21-25 |
| excellent | 6 | 26-30 |

The curling properties of the tested mascara products are described in Table 3.

TABLE 3

| The curling effect of tested mascara compositions | | | | | | |
|---|---|---|---|---|---|---|
| Curling | control 1 | Control 2 | inventive 1 | inventive 2 | Comparator 1 | Comparator 2 |
| Initial curl | 10-20° | 10-20° | 25-30° | 20-25° | 0-5° | 20-25° |
| Curl after 10 minutes | 0-5° | 10-20° | 25-30° | 20-25° | 0-5° | 20-25° |
| Initial curl | 2 | 2 | 5 | 4 | 1 | 4 |
| Curl after 10 minutes | 1 | 2 | 5 | 4 | 1 | 4 |

As is shown in Table 3 the inventive compositions containing both, thermoplastic elastomer and semi-crystalline acid appeared to have very good initial curling properties in comparison to both controls (control 1 and 2). In addition, both inventive compositions kept the initial level of curl within ten (10) minutes. Nevertheless, the eyelashes treated with control 1 did not hold the curl through the testing time.

Further, both inventive compositions had comparable curling properties when compared to comparator B and outperformed comparator A. The improved curling effect of the inventive compositions was observed immediately after treatment and also over 10 minutes of the testing time.

What is claimed is:

1. A cosmetic composition comprising: at least one thermoplastic elastomer in an amount of about 2 to about 40% by weight, relative to the total weight of the composition comprising a hydrogenated styrene/isoprene copolymer; at least one semi-crystalline polymer in an amount from about 0.1% to about 20%, by weight, relative to the total weight of the composition and comprising a poly C14 to C30 saturated alkyl (meth)acrylate and having a melting point of at least about 66° C.; and at least one organic solvent, wherein when said composition is applied to eyelashes it provides an initial curl that is maintained after 10 minutes.

2. The composition of claim 1, wherein the at least one organic solvent is present in an amount from about 4% to about 99%, by weight, relative to the total weight of the composition.

3. The composition of claim 1, wherein the composition is a mascara composition essentially free of wax.

4. The composition of claim 1, wherein the at least one organic solvent is selected from non-aromatic hydrocarbon oils and non-aromatic silicone oils.

5. The composition of claim 4, wherein at least one non-aromatic hydrocarbon oil is selected from isododecane, isodecane, isohexadacane, and mixtures thereof.

6. The composition of claim 1, further comprising a pigment in an amount from about 5% to about 15%, by weight, relative to the total weight of the composition.

7. A method of making the mascara composition of claim 6, the method comprising combining
   the at least one thermoplastic elastomer;
   the at least one semi-crystalline polymer;
   the at least one organic solvent; and
   the at least one pigment.

8. A method of curling eyelashes comprising applying the composition of claim 1 to eyelashes.

9. The composition of claim 1, wherein the at least one semi-crystalline polymer is present in an amount of about 1 to about 5% by weight, relative to the total weight of the composition.

10. The composition of claim 1, wherein the at least thermoplastic elastomer is present in an amount of about 3 to about 10% by weight, relative to the total weight of the composition.

11. The composition of claim 9, wherein the at least thermoplastic elastomer is present in an amount of about 3 to about 10% by weight, relative to the total weight of the composition.

* * * * *

UNITED STATES PATENT AND TRADEMARK OFFICE
CERTIFICATE OF CORRECTION

Page 1 of 1

PATENT NO. : 10,441,525 B2
APPLICATION NO. : 15/138073
DATED : October 15, 2019
INVENTOR(S) : Christopher Pang et al.

It is certified that error appears in the above-identified patent and that said Letters Patent is hereby corrected as shown below:

On the Title Page

In Column 2, item [56], Lines 1-3, delete
"http://www.bisi.cz/cmsres.axd/get/cms$7CVwRhc3USVqgzxkKF96gl$2BPpOqbtVs75H
RTjLxXUpZvBPQ97RI1thTexlHls7NqNufgyMPfh7fnpaFiNEaHYRNw$3D$3D" and insert
--http://www.bisi.cz/cmsres.axd/get/cms$7CVwRhc3USVqgzxkKF96gI$2BPpOqbtVs75H
RTjLxXUpZvBPQ97RI1thTexlHIs7NqNufgyMPfh7fnpaFiNEaHYRNw$3D$3D--.

In the Claims

Column 13, Line 18, Claim 5, delete "isohexadacane," and insert --isohexadecane,--.

Signed and Sealed this
Twenty-fourth Day of March, 2020

Andrei Iancu
*Director of the United States Patent and Trademark Office*